United States Patent [19]

Harker et al.

[11] 4,206,214

[45] Jun. 3, 1980

[54] ANTITHROMBOTIC PHARMACEUTICAL COMPOSITIONS CONTAINING DIPYRIDAMOLE AND SULFINPYRAZONE

[75] Inventors: Laurence A. Harker, Seattle, Wash.; Hans W. Schröter, Biberach, Fed. Rep. of Germany; Walter Haarmann, Biberach, Fed. Rep. of Germany; Josef Roch, Biberach, Fed. Rep. of Germany

[73] Assignee: Boehringer Ingelheim GmbH, Ingelheim, Fed. Rep. of Germany

[21] Appl. No.: 929,940

[22] Filed: Aug. 1, 1978

[30] Foreign Application Priority Data

Aug. 9, 1977 [DE] Fed. Rep. of Germany ....... 2735830

[51] Int. Cl.$^2$ ................. A61K 31/415; A61K 31/505
[52] U.S. Cl. ................................ 424/251; 424/273 P
[58] Field of Search ............................... 424/251, 273

[56] References Cited

U.S. PATENT DOCUMENTS

| 3,031,450 | 4/1962 | Fischer et al. | 544/81 |
| 3,322,755 | 5/1967 | Roch et al. | 424/251 |
| 3,562,265 | 2/1971 | Murakami et al. | 424/251 |

OTHER PUBLICATIONS

Helv. Chim. Acta., 44, 236 (1961).
Therapeiwoche, 26, 8464–8489 (1976).

*Primary Examiner*—Douglas W. Robinson
*Attorney, Agent, or Firm*—Hammond & Littell, Weissenberger & Muserlian

[57] ABSTRACT

Pharmaceutical dosage unit compositions containing, as a combination of active ingredients, dipyridamole and sulfinpyrazone, and a method of using the same as antithrombotics.

3 Claims, No Drawings

ANTITHROMBOTIC PHARMACEUTICAL COMPOSITIONS CONTAINING DIPYRIDAMOLE AND SULFINPYRAZONE

This invention relates to antithrombotic pharmaceutical dosage unit compositions containing, as a combination of active ingredients, dipyridamole and sulfinpyrazone, as well as to a method for preventing or relieving thrombosis therewith.

BACKGROUND OF THE INVENTION 2,6-Bis-(diethanolamino)-4,8-dipiperidino-pyrimido-[5,4-d]-pyrimidine (generic name: Dipyridamole) has for a long time been used as a coronary dilator; it was first described in British Pat. No. 807,826. Likewise, 1,2-diphenyl-3,5-dioxo-4-(2-phenylsulfinyl-ethyl)-pyrazolidine (generic name: Sulfinpyrazone) has for a long time been used as an anti-gout agent; it was first described in Helv. chim. Acta. 44, 236 (1961). Both therapeutics were subsequently also found to have a good antithrombotic effect; see, for example, Therapiewoche 26, 8464–8489 (1976).

In the case of both substances, however, a relatively high dosage is required for of an antithrombotic effect, where certain side-effects of both compounds become noticeable; with diphyridamole the side effects are certain circulatory effects which show themselves as headaches; with sulfinpyrazone they are stomach pains due to the ulcerogenic effect of this substance at high dosages.

The Invention

We have discovered that when dipyridamole and sulfinpyrazone are administered together to a warm-blooded animal, a strong synergistic antithrombotic effect is produced, whereby the individual dosages of the two compounds required for achievement of the same antithrombotic effect produced by each of them alone can be substantially reduced. This synergistic effect was ascertained in the following experimental mode in baboons:

An A-V-shunt was applied between arteria and vena fermoralis of anesthetized male baboons with a body weight of 8–12 kg. This shunt was about 50 cm long and consisted of a specially prepared Silastik hose. The stimulus of the hose surface, which is foreign to the organism, causes an increased thrombocyte consumption, because the organism seeks to cover up this "defect". This effect can easily be measured by injecting the test animals with thrombocytes labeled with radioactive chromium 51 and monitoring their disappearance from the blood stream by twice daily measurements. With a normal thrombocyte consumption the life of the thrombocytes is about 5 days, but in the case of the animals equipped with the shunt, the average life of the thrombocytes (as a sign of an increased thrombocyte consumption) is shorted to about 2–2.5 days.

During the test the test compounds were orally administered individually and in combination to the awake animals over the test period of 4–5 days four times daily.

The results obtained with this method are shown in the following table:

| Effect of Combination of Dipyridamole with Sulfinpyrazone in Baboons Survival time of thrombocytes (in days) | | | | | | | |
|---|---|---|---|---|---|---|---|
| Animal No. | Control | Starting value of animal with applied shunt | Dipyridamole alone | | Sulfinpyrazone alone | | dipyridamole and sulfinpyrazone together 2.5 mgm/kg/day each |
| | | | 2.5 mgm/kg/day | 10 mgm/kg/day | 2.5 mgm/kg/day | 100 mgm/kg/day | |
| 1 | 5.5 | 2.0 | 2.4 | 5.1 | 1.9 | 5.3 | 4.9 |
| 2 | 5.1 | 2.7 | 2.6 | 4.9 | 2.8 | 4.7 | 5.3 |
| 3 | 5.4 | 2.3 | 2.3 | 5.6 | 2.7 | 5.0 | 5.1 |
| 4 | 5.6 | 2.9 | 3.3 | 5.3 | 2.4 | 5.3 | 5.0 |
| 5 | 5.2 | 2.5 | 3.1 | 5.0 | 2.9 | 4.9 | 4.7 |
| Average Value | 5.4 ± 0.4 | 2.5 ± 0.4 | 2.9 ± 0.4 $p<0.05$ | 5.2 ± 0.3 $p<0.001$ | 2.5 ± 0.4 $p\leqq0.50$ | 5.0 ± 0.3 $p<0.001$ | 5.0 ± 0.2 $p<0.001$ | p = statistical probability

The table clearly shows that for normalization of the shortened thrombocyte life time 10 mgm/kg/day of dipyridamole or 100 mgm/kg/day of sulfinpyrazone are required, but that the same effect is achieved with a combination of 2.5 mgm/kg/day of each of the two active substances. It is known that the results regarding normalization of the thrombocyte life time in the monkey can be very well transferred to humans; for instance, the same dose of dipyridamole per kilogram is required for achievement of the same effect in men as in the monkey. The normalization of the thrombocyte life time is therapeutically of very great importance because the shortening of the thrombocyte life time which occurs in humans is an indication of a tendency toward thromboses. Therefore, the novel drug combination is well suited for the prevention and cure of thromboembolic diseases.

A single dose for adults contains between 25 mgm (about 0.3 mgm/kg) and 75 mgm (about 1.0 mgm/kg) of the two active substances, preferably 50 mgm dipyridamole and 50 mgm sulfinpyrazone; the single dose is preferably administered three times daily, so that the average daily dose is 150 mgm or about 2.5 mgm/kg of each of the two active substances. Since both active substances have already been in commerce for many years, no disclosure needs to be made about toxicity because it is known to be low in both cases.

A further object of the invention is a process for the manufacture of the drug combination according to the invention, which comprises combining 2,6-bis-(diethyanolamino)-4,8-dipiperidino-pyrimido [5,4-d] pyrimidine and 2,6-diphenyl-3,5-dioxo-4-(2-phenylsulfinyl-ethyl)-pyrazolidine in a weight ratio of from 10:1 to 1:10, preferably 1:1, and formulating the combination optionally with other active substances, with inert pharmaceutical carriers and/or excipients conventional in the preparation of drugs into conventional pharmaceutical dosage unit compositions, such as tablets, coated pills, powders, capsules and the like. The combination according to the invention is preferably administered perorally.

The manufacture of tablets, coated pills, capsules, etc. is effected in known manner; for example, the tablets are prepared by direct compression of a mixture of the active ingredients and the excipients and are optionally subsequently coated with a thin shell which is compatible with the stomach and the intestine; in the manufacture of the capsules, first the powder mixture and the core with the coating are separately prepared and then filled in a commercial capsule filling machine.

The following examples illustrate a few antithrombotic pharmaceutical dosage unit compositions comprising the combination of active ingredients of the present invention and represent the best modes contemplated of using the invention. The parts are parts by weight unless otherwise specified.

EXAMPLE 1

Coated pills

The pill core composition is compounded from the following ingredients:

| | |
|---|---|
| Dipyridamole | 50.0 parts |
| Sulfinpyrazone | 50.0 parts |
| Lactose | 187.0 parts |
| Corn Starch | 105.0 parts |
| Gelatin | 6.0 parts |
| Magnesium stearate | 2.0 parts |
| Total | 400.0 parts |

Preparation

The active ingredients are admixed with the lactose and the corn starch, and the mixture is uniformly moistened with an aqueous solution of the gelatin. The moist mass is granulated by passing it through a 2 mm-mesh screen, the granulate is dried, and the dry granulate is again passed through the screen and then admixed with the magnesium stearate. The composition is compressed into 400 mgm pill cores which are subsequently coated in conventional manner with a thin shell consisting essentially of a mixture of sugar and talcum. Each coated pill is an oral dosage unit composition containing 50 mgm of dipyridamole and 50 mgm of sulfinpyrazone.

EXAMPLE 2

Hard gelatin capsules

The capsule filler composition, consisting of a powder and a coated pellet, is compounded from the following ingredients:

| (a) Powder | |
|---|---|
| Sulfinpyrazone | 50.0 parts |
| Corn starch | 158.0 parts |
| Lactose, powdered | 90.0 parts |
| Magnesium stearate | 2.0 parts |
| Total | 300.0 parts |

Preparation:

The ingredients are admixed, and the mixture is milled into a homogeneous powder.

| (b) Coated pellet | |
|---|---|
| Dipyridamole | 50.0 parts |
| Polyvinylpyrrolidone | 2.5 parts |
| Formaldehyde gelatin | 6.5 parts |
| Magnesium stearate | 1.0 parts |
| Lactose | 25.0 parts |
| Total | 85.0 parts |

Preparation

The ingredients are compounded in the same way as in Example 1, and the composition is compressed into 85 mgm-pellets which are subsequently coated with a shell consisting essentially of a mixture of talcum, sugar and gum arabic.

300 mgm-portions of the powder together with one coated pellet are filled into size O hard gelatin capsules. Each capsules is an oral dosage unit composition containing 50 mgm of dipyridamole and 50 mgm of sulfinpyrazone.

The amounts and ratios of active ingredients in these illustrative examples may be varied to achieve the ranges set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. An antithrombotic pharmaceutical composition consisting essentially of an inert pharmaceutical carrier and an antithrombotic effective amount of a mixture of a dipyridamole and sulfinpyrazone wherein the weight ratio of dipyridamole and sulfinpyrazone is 1:1.

2. The method of preventing or relieving thrombosis in a warm-blooded animal, which comprises perorally administering to said animal an antithrombotic effective amount of a mixture of dipyridamole and sulfinpyrazone wherein the weight ratio of diphyridamole and sulfinpyrazone in said mixture is 1:1.

3. The composition of claim 1 in unit dosage form.

* * * * *